(12) United States Patent
Tennican

(10) Patent No.: US 9,527,660 B2
(45) Date of Patent: Dec. 27, 2016

(54) INDIVIDUALLY SEALED ANTISEPTIC APPLICATORS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 0 days.

(21) Appl. No.: 14/588,229

(22) Filed: Dec. 31, 2014

(65) Prior Publication Data
US 2016/0185514 A1    Jun. 30, 2016

(51) Int. Cl.
| | | |
|---|---|---|
| *A61M 39/16* | (2006.01) | |
| *B65D 85/00* | (2006.01) | |
| *B65D 77/04* | (2006.01) | |
| *B65D 77/20* | (2006.01) | |

(52) U.S. Cl.
CPC ............ *B65D 85/70* (2013.01); *B65D 77/048* (2013.01); *B65D 77/2032* (2013.01)

(58) Field of Classification Search
USPC ...... 220/23.87; 206/363, 460, 461; 604/533, 604/539; 15/104.011
See application file for complete search history.

(56) References Cited

U.S. PATENT DOCUMENTS

| | | | | |
|---|---|---|---|---|
| 4,667,837 A | * | 5/1987 | Vitello | A61M 5/5086 206/445 |
| 7,243,796 B2 | * | 7/2007 | Grablick | 206/460 |
| 2009/0028750 A1 | * | 1/2009 | Ryan | 422/28 |
| 2011/0052664 A1 | * | 3/2011 | Tennican et al. | 424/445 |

FOREIGN PATENT DOCUMENTS

JP          07061482 A  *  3/1995  ............. B65D 81/28

OTHER PUBLICATIONS

JP_07-061482_Description_of_Drawings.pdf.*
JP_07-061482_Detailed_Description.pdf.*
PCT Search Report and Written Opinion mailed Mar. 11, 2016 for PCT application No. PCT/US15/68138, 11 pages.

* cited by examiner

*Primary Examiner* — J. Gregory Pickett
*Assistant Examiner* — Allan Stevens
(74) *Attorney, Agent, or Firm* — Lee & Hayes, PLLC

(57) ABSTRACT

This disclosure describes example applicators and cap devices which may be used in combination with one or more cleansing, antimicrobial and/or antiseptic agents to reduce or eliminate contaminates on a surface. According to some embodiments, the disclosure describes a first cap which may be stored within a cavity of a second cap to create a dual cap device. According to some embodiments, both caps of the dual cap device may be individually sealed with a protective film. According to some embodiments, either a single cap device or a dual cap device may be attached to a flexible substrate by a surface other than the surface having the cavity opening.

19 Claims, 6 Drawing Sheets

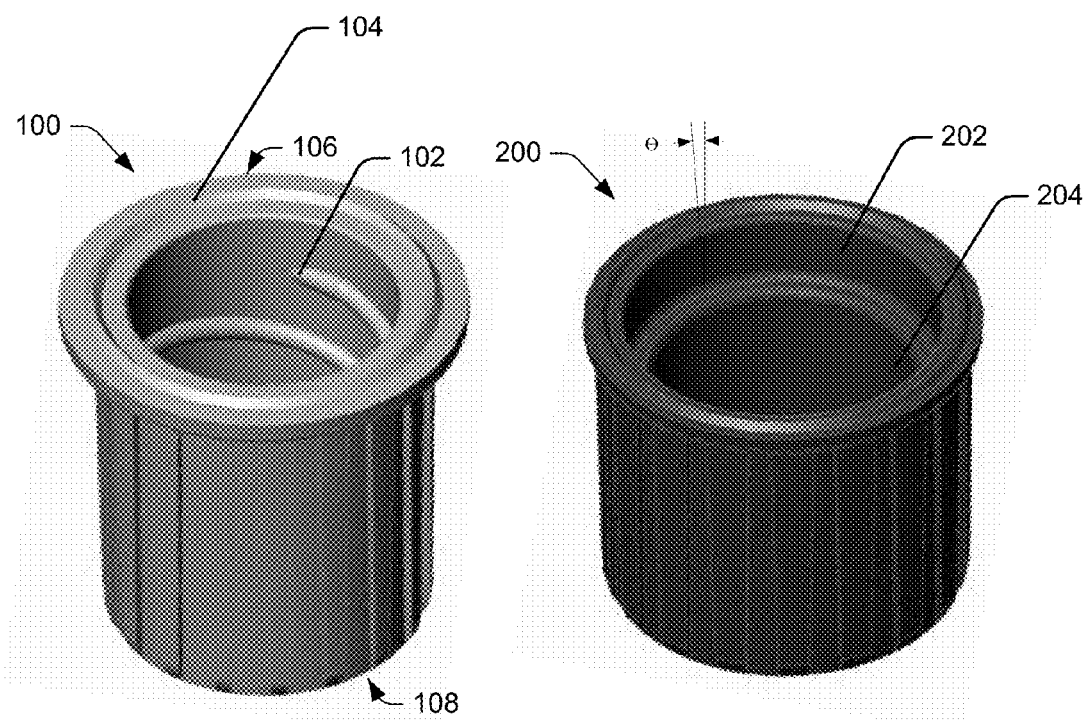
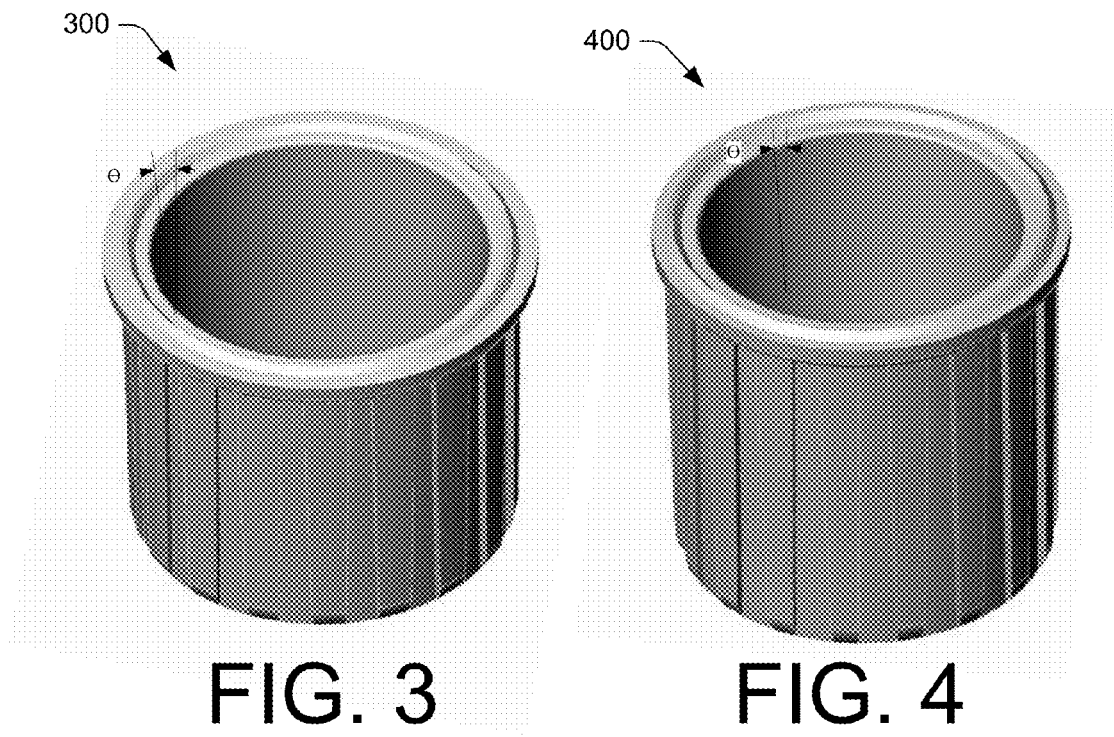

though the page number says "US 9,527,660 B2" — omitting per rules.

INDIVIDUALLY SEALED ANTISEPTIC APPLICATORS

BACKGROUND

Healthcare acquired infection (HAI) has been recognized as a significant cause of preventable mortality and morbidity. In some instances, HAIs may be acquired by the introduction of microorganisms into an intravenous (IV) line, such as a peripheral IV line and central IV line. For instance, microorganisms present on a surface of an injection port of the IV line may be introduced into a patient during the preparation or initiation of fluid administration into or withdrawal from the IV line. Accordingly, it may be advantageous to develop methods and devices for cleaning of external surfaces of IV access ports and/or internal port areas to reduce risks of microorganism colonization and infection. In addition, it may be advantageous to develop methods and devices for capping the external surfaces of IV access ports and/or internal port areas to reduce risks of microorganism colonization and infection.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIGS. 1-4 illustrate example applicators and cap devices which may be used in a single cap device or a dual cap device.

DETAILED DESCRIPTION

Overview

Figure 5:
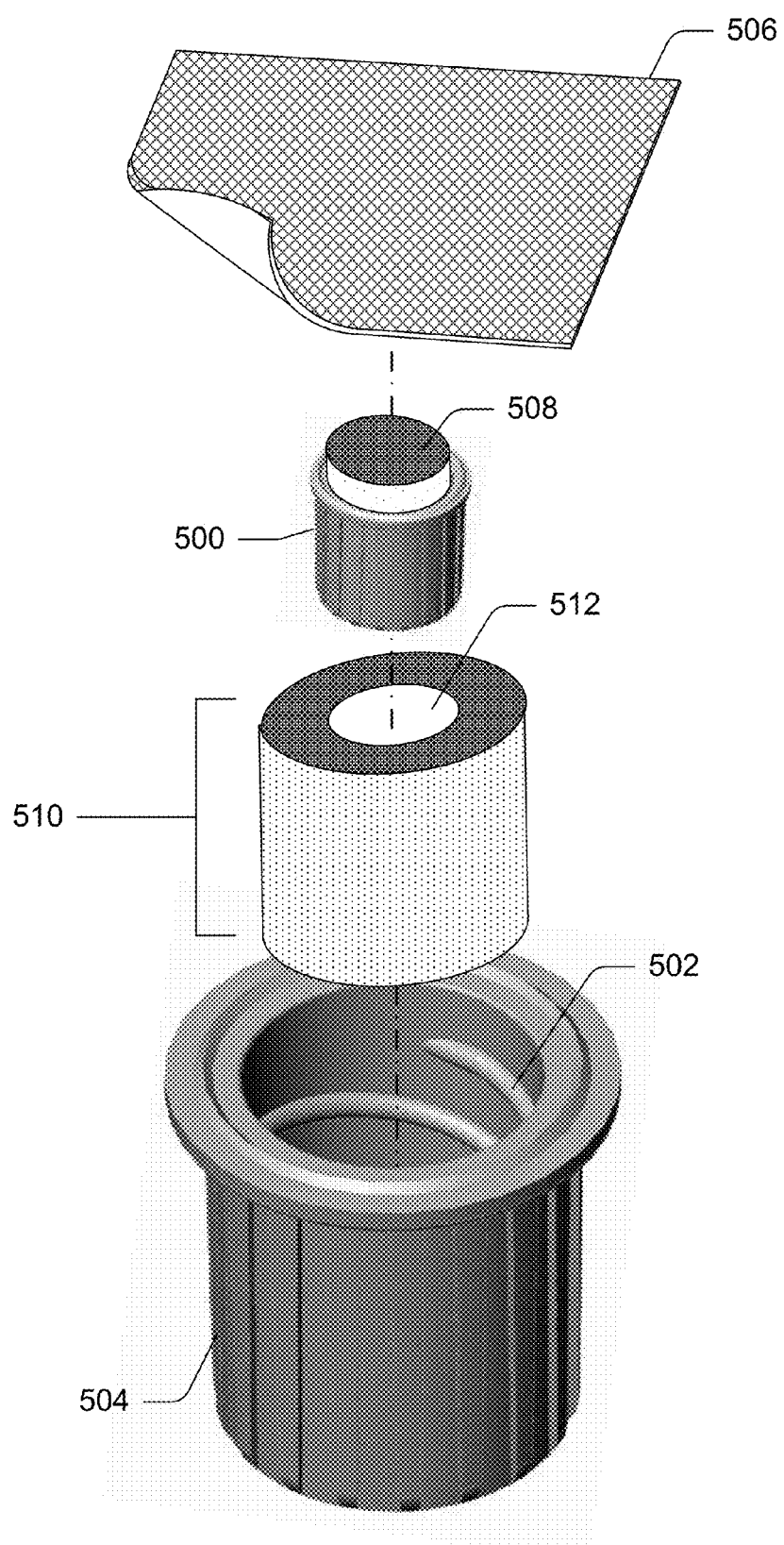
FIGS. 5-7 illustrate example embodiments of individually sealed applicators and cap devices used in dual cap devices.

This disclosure describes medical applicators and protective cap devices designed to reduce and/or prevent infections. In one embodiment, the disclosure describes individually sealed applicators and cap devices. In other embodiments, the disclosure describes dual cap devices comprising the individually sealed applicators and cap devices. The individually sealed applicators and cap devices may include a permeable foam applicator material that may be coated or filled with, for example, a cleansing, antiseptic or antimicrobial composition. In some embodiments, an open end of each individually sealed applicator and cap device may be sealed with a removable protective film or cover to maintain the applicator material and cleansing, antimicrobial, or antiseptic composition in the respective caps. In some embodiments, a surface other than the open end (i.e. a top end) of individually sealed applicators and cap devices or dual cap devices may be consecutively adhered or bonded directly to a substrate such as, for example, a tape or strip.

In other embodiments, the disclosure describes applicators and cap devices which may include an external cap device configured to hold or store an internal cap device within a cavity of the external cap device. In some embodiments, the each applicator or cap device may be individually sealed. In other embodiments, only the external cap device may be sealed over the open end with a removable protective film or cover to maintain the internal cap device, an applicator material and/or cleansing, antimicrobial, or antiseptic composition in the respective cap devices. In some embodiments, a surface other than the open end of external cap device may be coupled or bonded directly to a substrate such as, for example, a tape or strip with a plurality of other cap devices. For example, a top end of each cap device may be consecutively adhered to a roll-able strip.

This overview, including section titles, is provided to introduce a selection of concepts in a simplified form that are further described below. The overview is provided for the reader's convenience and is not intended to limit the scope of the claims, nor the proceeding sections.

Example Composition

In one example embodiment, antimicrobial or antiseptic compositions that may be used in connection with the approaches described herein may include those described in, for example, U.S. Provisional Patent Application No. 61/412,375, filed Nov. 10, 2010 to Tennican et al., which is incorporated herein by reference. For example, the antimicrobial compositions may include water ($H_2O$), a strong and non-toxic chelating agent such as ethylenediaminetetraacetic acid (EDTA)(e.g., disodium EDTA, calcium disodium EDTA, magnesium EDTA, potassium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. Additional ingredients can include thickeners, gellants (e.g., hydroxypropyl methylcellulose (HPMC), carboxymethyl cellulose (CMC), methyl cellulose, methyl hydroxyethyl cellulose (MHEC), hydroxyethyl cellulose, sodium hydroxyalkyl cellulose, dimethicone, silicone gel, or combinations thereof), surfactants, foamers and/or foam stabilizers. However, in other examples, other antimicrobial compositions may be used in combination with the applicators and devices described in this disclosure.

In some embodiments, the antimicrobial composition may include from water; from about 20% to about 70% by volume of ethanol; from about 0.5% to about 7.5% by volume of hydrogen peroxide; from about 5 mg/mL to about 50 mg/mL of ethylenediamine tetraacetic acid (EDTA), acids of EDTA, salts of EDTA, citrate, salts of citrate or any combination thereof.

The antimicrobial compositions may be in a liquid form or a gel form, and may be combined with one or more carriers or diluents, depending on the needs of a specific application. For example, if the antimicrobial composition is used as a cleaning agent the antimicrobial composition may be in a liquid form. In that case, the concentration of the various constituents may depend on, for example, a desired level of sanitation and/or disinfection, whether the composition is being applied directly to living tissue or to a medical device, and/or avoidance of irritation of tissue to which the composition will be applied directly or indirectly (e.g., via a medical device to which the composition is or was applied).

In addition to providing disinfection at the time of the application, the antimicrobial compositions may also provide a lasting barrier against contamination. For example, even after volatile constituents of the composition (e.g., water, alcohol, hydrogen peroxide, etc.) have evaporated, the chelating agent may remain on the treated surfaces (e.g., multiple use vial or port cleaning/protecting device, stethoscope, fingers, surrounding tissue, etc.) as a barrier that will provide antibacterial, antifungal or sporicidal (e.g., preventing germination of the spores), anti-parasitic, spermicidal or spermiostatic (e.g., decrease the motility of spermatozoon) and antiviral qualities. By robbing the environment of components (e.g., iron, magnesium, and manganese) that are needed for the bacteria, spores, parasites, fungus and viruses to reproduce, the chelating agent may provide a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

In some embodiments, the antimicrobial composition described above may also provide a visual indication of contamination when applied to a surface or material, such indication may allow users to identify and clean surfaces to prevent infection.

The term "about" or "approximate" as used in context of describing the example antimicrobial composition is to be construed to include a reasonable margin of error that would be acceptable and/or known in the art.

As used herein, the terms "a," "an," and "the" mean one or more.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description may use numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description may use specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values, but should also be applied to differences between these specific values.

Example Applicators and Cap Devices

FIGS. 1-4 illustrate several example applicators and cap devices. In each embodiment, the example applicators and cap devices may be configured to secure to medical instruments and/or laboratory equipment. For example, the example applicators and cap devices may be configured to connect to a syringe with a male or female LUER-LOK® connection fitting, a slip tip LUER-SLIP® fitting, a central or peripheral IV port, a catheter port (i.e., a peripherally inserted central catheter of a central venous catheter), PORT-A-OATH®, multi-dose vials, among others. While FIGS. 1-4 illustrate the example applicators and cap devices as having a generally round shape, alternative shapes are contemplated such as, for example, a square shape, a rectangular shape, an oval shape, a polygon shape, and the like. In addition, example applicators and cap devices may be manufactured in any size to accommodate the various sizes of the ports or connectors to which the applicators and cap devices may be attached.

Example materials for the composition of the example applicators and cap devices include, but are not limited to, polypropylene, polyethylene and/or other copolymer materials. The example applicators and cap devices may also comprise a material or agent that is UV protective to preserve the integrity of a composition, such as one described in the preceding section, during storage, shipping, etc. In other embodiments, the example applicators and cap devices may comprise caps such as those described in U.S. patent application Ser. No. 13/688,044, filed Nov. 28, 2012 to Tennican et al., entitled "Port and Surface Cleaning Devices and Techniques," which is incorporated herein by reference.

FIG. 1 illustrates a first example cap device 100. As shown in FIG. 1, the inner surface of the example cap device 100 includes threads 102 molded into the inner surface of the cavity. This attachment feature may allow the user to thread in a twisting motion the example cap device onto a surface such as a male LUER-LOK® connector, for example. FIG. 1 also illustrates cap device 100 having a flange 104 along the bottom surface (the bottom surface/end of cap device 100 designated with arrow 106 and the top surface/end of cap device designated with arrow 108) of the opening and extending away from the opening of the cap device. In some embodiments, the flange 104 may allow cap device 100 to secure to a surface such a female LUER-LOK® connector, for example.

FIG. 2 illustrates an example cap device 200 having a stepped inner surface, including a first inner surface 202 and a second inner surface 204, the second inner surface 204 having a smaller average diameter than the first inner surface. The first and second inner surfaces 202 and 204 may have diameters chosen to match outer diameter ("OD") of common medical equipment connectors on the market (i.e., LUER-LOK®), of maximum and minimum ODs of medical equipment connectors on the market, or based on other criteria. Further both of the first and second inner surfaces 202 and 204 may be tapered (i.e., have a draft angle θ), such that a diameter of the first and second inner surfaces is largest closest to an opening of the example cap device 200 and decreases toward the top, closed end of the example cap device 200. A draft angle of the first inner surface 202 may be the same as, greater than, or less than a draft angle of the second inner surface 204. When the example cap device 200 is placed on a surface of a medical connector, the example cap device 200 will slide over the surface until an OD of the surface contacts and seals against the interior surface of the example cap device 200 at either the first inner diameter 202 (in the case of a connector surface with a relatively large OD) or the second inner diameter 204 (in the case of a connector surface with a relatively small OD).

FIGS. 3 and 4 illustrate alternative embodiments of slip fit cap devices 300 and 400, respectively, which have continuous, smooth inner surfaces. Rather than being stepped as in the embodiment of FIG. 2, the protective cap devices 300 and 400 have continuous, smooth inner surfaces. The inner surfaces of the cap devices 300 and 400 are tapered to accommodate connector surfaces of varying OD. However, in order to accommodate connector surfaces having a wide range of ODs, the draft angle θ of the cap devices needs to be larger (i.e., a more pronounced taper) as in the case of protective cap device 300, and/or the protective cap device needs to be made deeper, as in the case of protective cap device 400.

In some embodiments, each of example cap devices 100, 200, 300, and/or 400 may be constructed with a flange on the inner surface at the opening of a cavity of the cap device. In this embodiment, the inner surface of the example cap device may otherwise have a continuous smooth surface. Furthermore, the size of the flange may vary depending, in part, on the OD of the connector surface to be attached to the cap device. When the example cap device in this embodiment is placed over the connector surface the flange allows the example cap device to snap into place over the connector surface.

Figure 6:
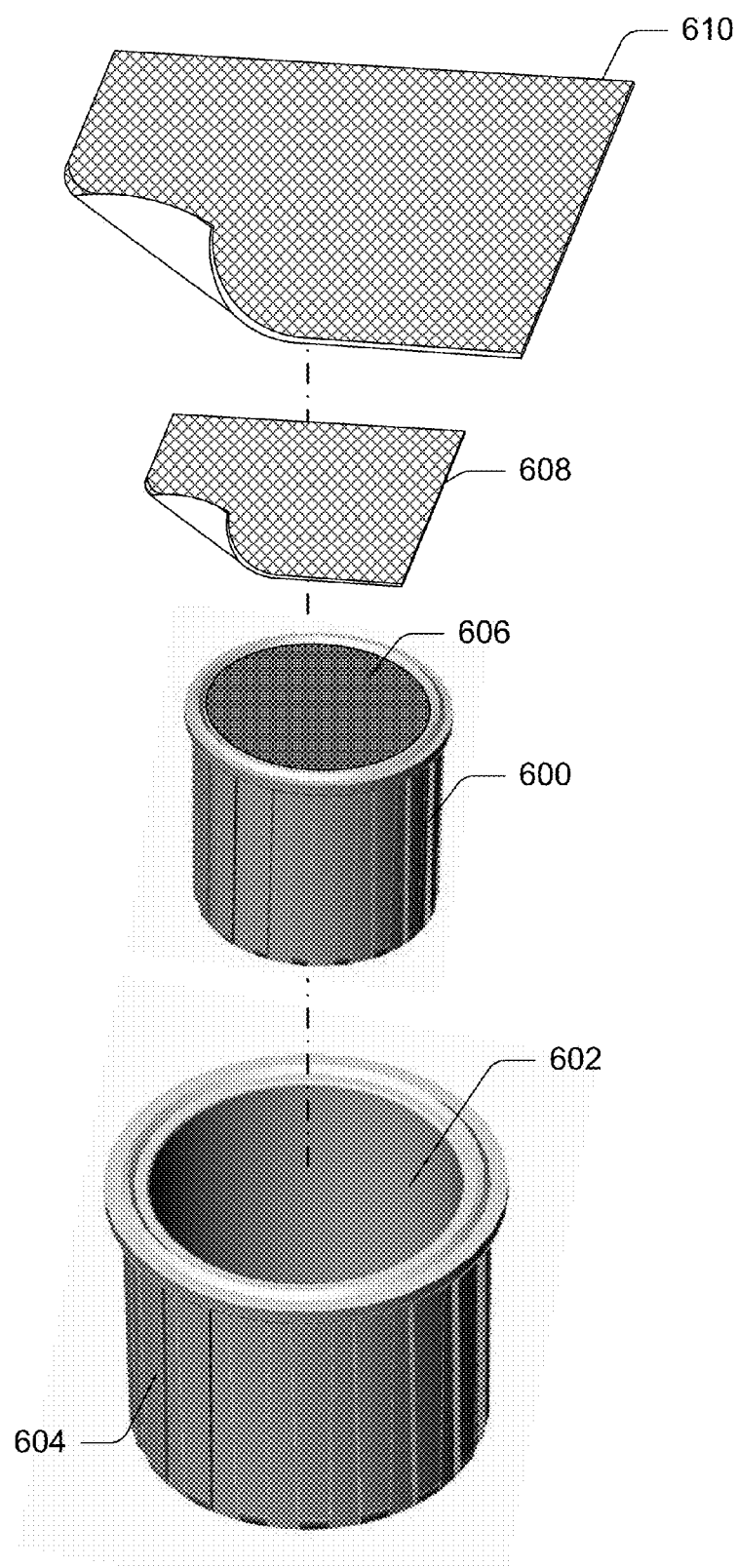
Figure 7:
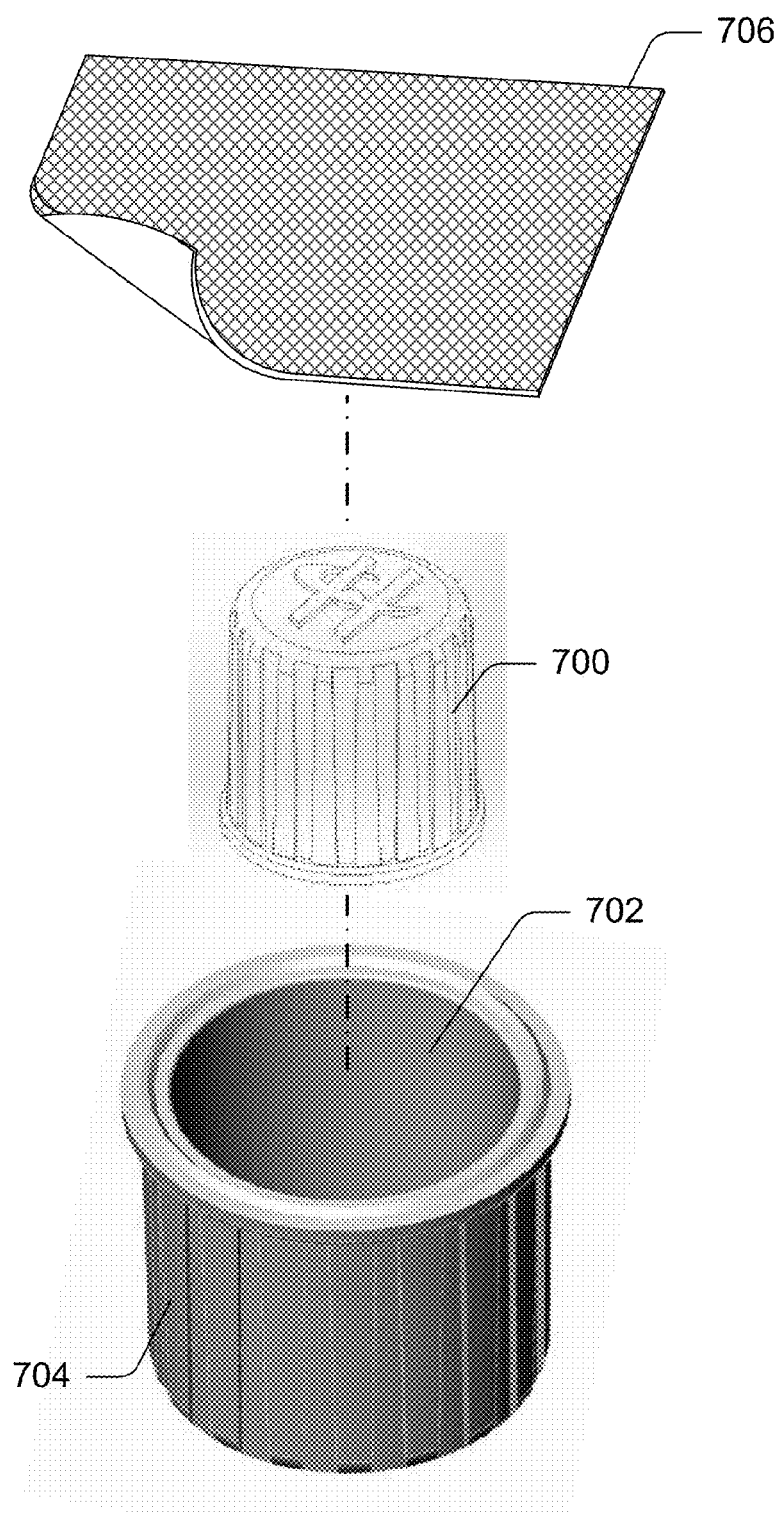

FIGS. 5-7 illustrate example embodiments of individually sealed applicators or cap devices which may form a dual cap device. In each example illustrated in FIGS. 5-7, a first applicator or cap device may be housed in a cavity of a second applicator or cap device. FIG. 5-7 illustrated specific applicators cap devices as described above with reference to FIGS. 1-4; however, it should be noted that FIGS. 5-7 are not limited to the specifically illustrated applicators or cap devices. For instance, any combination of the applicators and cap devices described above may be used in conjunction with the example embodiments of individually sealed applicators or cap devices to form a dual cap devices as discussed with reference to FIGS. 5-7.

FIG. 5 illustrates a first cap device 500 which may be removably stored within a cavity 502 of a second cap device 504. In some embodiments, the cavity 502 of the second cap 504 may be sealed by a removable protective film 506. The removable protective film 506, while in place over the cavity 502, may prevent the first cap device 500 and other contents such as an applicator material or antimicrobial composition from escaping. In some embodiments, the removable protective film 506 may be sealed around a periphery of the cavity 502 of the second cap device 504 by, for example, an adhesive (e.g., silicone, silicone rubber, synthetic resin, methyl methacrylate, for example), a thermoplastic, sonic welding, microwave welding, thermal bonding, induction heating, or the like. In some embodiments, the protective film 506 may be a gas/liquid impermeable, pore-free (i.e., thicker than 1 micron), flexible material such as aluminum oxide, silicon oxide, or the like.

FIG. 5 illustrates one example embodiment in which both the first cap device 500 and second cap device 504 include an applicator material 508 and 510, respectively, disposed within a cavity of each cap device, such a cavity 502 of second cap device 504. Applicator material 508 and 510 (or any other described herein) may be an open-celled, permeable foam or sponge material, that may be coated or impregnated with a cleansing, antimicrobial, or antiseptic composition such as those described in the preceding section. Example materials for the composition of the applicator material 508 and 510 may include, but are not limited to starch polymer, cellulosic gel, polyurethane, silicon, silicon rubber, polyethylene, polypropylene, thermoplastic elastomer or mixtures thereof. In some embodiments, when the first cap device 500 is stored within the second cap device 504, the applicator material 508 may be in a state of compression. In some embodiments, the applicator material 508 may expand and/or protrude from the interior cavity of the first cap device 500 for use in cleaning or disinfecting a desired site surface (e.g., for disinfecting a intravascular port line, site preparation for a medical procedure, or the like). In some embodiments, the applicator material may include a closed-cell region on one or both axial ends of the applicator material. In some embodiments, the closed-cell region may have different surface finishes, treatments, or contours (e.g., macro-, micro-, or nano-structures, etc.) to facilitate gripping and/or scrubbing of a surface.

In some embodiments, the applicator material 510 housed within cavity 502 of the second cap device 504 may include an opening 512 to secure the first cap device 500. In some embodiments, opening 512 may be a diameter smaller than the outer diameter of the first cap device 500. While opening 512 is illustrated as generally circular, the opening 512 may be any suitable shape to secure or hold a first cap device of any size or shape. For example, opening 512 may be a polygon. Furthermore, in some embodiments, the opening 512 may be configured as a cone where the diameter of base of cone, which may be positioned toward the external portion of the application material 510, is slightly smaller than a diameter of the first cap device 500 and the diameter of the cone tapers toward the apex of the cone, which may be positioned toward the internal portion of the application material 510.

In some embodiments, the applicator material 508 and/or 510 may include, but are not limited to, different surface treatments (e.g., siping, slitting, etc.), surface finishes (e.g., macro-, micro-, or nano-structures, etc.), and/or contours (e.g., rounded, ribbed, protrusions, fingers, etc.) to provide cleaning and/or scrubbing effectiveness. In some embodiments, applicator material 508 in the first cap device 500 may be configured similar to the applicator material 510 in the second cap device 504 (e.g., with the same surface treatments, finishes and/or contours). However, in other embodiments, the applicator material 508 in the first cap device 500 may be configured with a different surface treatments, finishes and/or contours than the applicator material 510 in the second cap 504.

In some embodiments, each cap device 500 and 504 may be individually sealed by a removable protective film or cover over a cavity that maintains the applicator material 508 and 510, respectively, and a cleansing, antimicrobial, or antiseptic composition in the respective cap device. In some embodiments, each applicator material 508 and 510 of each cap device may contain a different cleansing, antimicrobial or antiseptic composition and/or different concentration of such composition.

FIG. 5 illustrates the applicator material 508 of the first cap device 500 may protrude from the cavity of the cap device, while the applicator material 510 of the second cap device 504 fits completely within and/or is recessed in a cavity 502 in the cap device when in use. In that case, the first cap device 500 with the protruding applicator material 508 may be used to clean a surface (e.g., an intravascular line, valve, or port, an injection site, or the like) and the second cap device 504 with the recessed applicator material 510 may be used to connect to and protect an port, vial, syringe, or other component (e.g., an intravascular line port, a catheter, or the like).

In some embodiments, where the first cap device or second cap device may be configured to connect to and/or protect a surface as described above, each of the first and second cap devices may have one of various example mechanisms for attaching each cap to the surface as described above in FIGS. 1-4.

FIG. 6 illustrates another example embodiment in which a first cap device 600 may be removably stored within a cavity 602 of a second cap device 604. FIG. 6 illustrates the first cap device 600 and the second cap device 604 similar to the cap device illustrated in FIGS. 3 and 4, respectively. However, the first cap device and the second cap device may be any combination of the cap devices described above with regard to FIGS. 1-4.

As shown in FIG. 6, the first cap device 600 may include an applicator material 606 within a cavity of the first cap device. Details of the applicator material are discussed above with regard to FIG. 5. In some embodiments, both, neither, or any combination thereof of the first cap device 600 and the second cap device may have an applicator material. In some embodiments, the applicator material may be coated or saturated with a composition such as an antimicrobial solution.

In some embodiments, the first cap device 600 may be sealed with a protective film 608. Details of the protective film are discussed above with regard to FIG. 5. In some embodiments, the protective film 608 may create a liquid and/or gas impermeable barrier to contain the applicator material 606 and/or any composition within the cavity of the first cap device 600.

In some embodiments, the individually sealed first cap device 600 may be configured to fit within the second cap device 600 such that the first cap device is completely within the cavity 602 of the second cap device 604. In other embodiments, the first cap device 600 may be configured to partially fill the cavity 602 of the second cap device 604.

In some embodiments, the cavity 602 of the second cap device 604 may be treated or coated with a composition such as an antimicrobial solution. In some embodiments, the cavity 602 of the second cap device 604 may include an applicator material which may be coated or saturated with a composition such as an antimicrobial solution.

FIG. 6 illustrates a second protective film 610 which may be removably attached to the flange of the second cap device 604. In some embodiments, the second protective film 610 may create a barrier holding the individually sealed first cap device 600 within the cavity 602 of the second cap device 604. In some embodiments, the protective film 608 on the first cap device 600 and the second protective film 610 on the second cap device 604 may be composed of the same material. However, in other embodiments, the protective films 608 and 610 may be composed of different material depending on the contents (i.e., applicator material, composition, other caps) of the cavity of the respective cavities of the cap devices and/or the type of mechanism of sealing the protective film (i.e., sonic welding, microwave welding, thermal bonding, or the like).

In some embodiments, the protective film 610 may be removed from the second cap device 604 to expose the cavity 602. Within the cavity 602, may be the first cap device 600 individually sealed with the protective film 608. In some embodiments, the first cap device 600 may be removed from the cavity 602 of the second cap device 604. In some embodiments, the first cap device 600 and/or the second cap device 604 (which may include an applicator material (not shown)) may then be used to clean and/or protect a surface such as a port, vial, syringe, or other component (e.g., an intravascular line port, a catheter, or the like). In some embodiments, the first cap device 600 and/or second cap device 604 may securely attach to the surface. In some embodiments, the first cap device 600 may be used to clean the surface while the second cap device 604 may subsequently be placed over the surface to protect the surface from recontamination.

In some embodiments, the protective film 608 may be removed from the first cap device 600 to expose the applicator material 606 and/or compositions therein. The first cap device 600 may then be used to clean and/or protect a surface such as a port, vial, syringe, an injection site, or other component (e.g., an intravascular line port, a catheter, or the like). In some embodiments, the first cap device 600 may securely attach to the surface.

FIG. 7 illustrates another example embodiment in which a first cap device 700 may be removably stored within a cavity 702 of a second cap device 704. FIG. 7 illustrates the second cap device 704 similar to the cap device illustrated in FIG. 3. However, the first cap device 700 and the second cap device 704 may be any combination of the cap devices described above with regard to FIGS. 1-4.

As shown in FIG. 7, the first cap device 700 may be configured to fit into the cavity 702 of the second cap device 704 while the protective film 706 may removably seal to the flange of the second cap device 704 to secure the first cap device 700 within at least a part of the cavity 702. In some embodiments, a cavity of the first cap device 700 and/or cavity 702 of the second cap device 704 may have an applicator material and/or composition as described above. In some embodiments, the first cap device 700 may also include a protective film over the cavity while secured in the cavity 702 of the second device 704.

Figure 8:
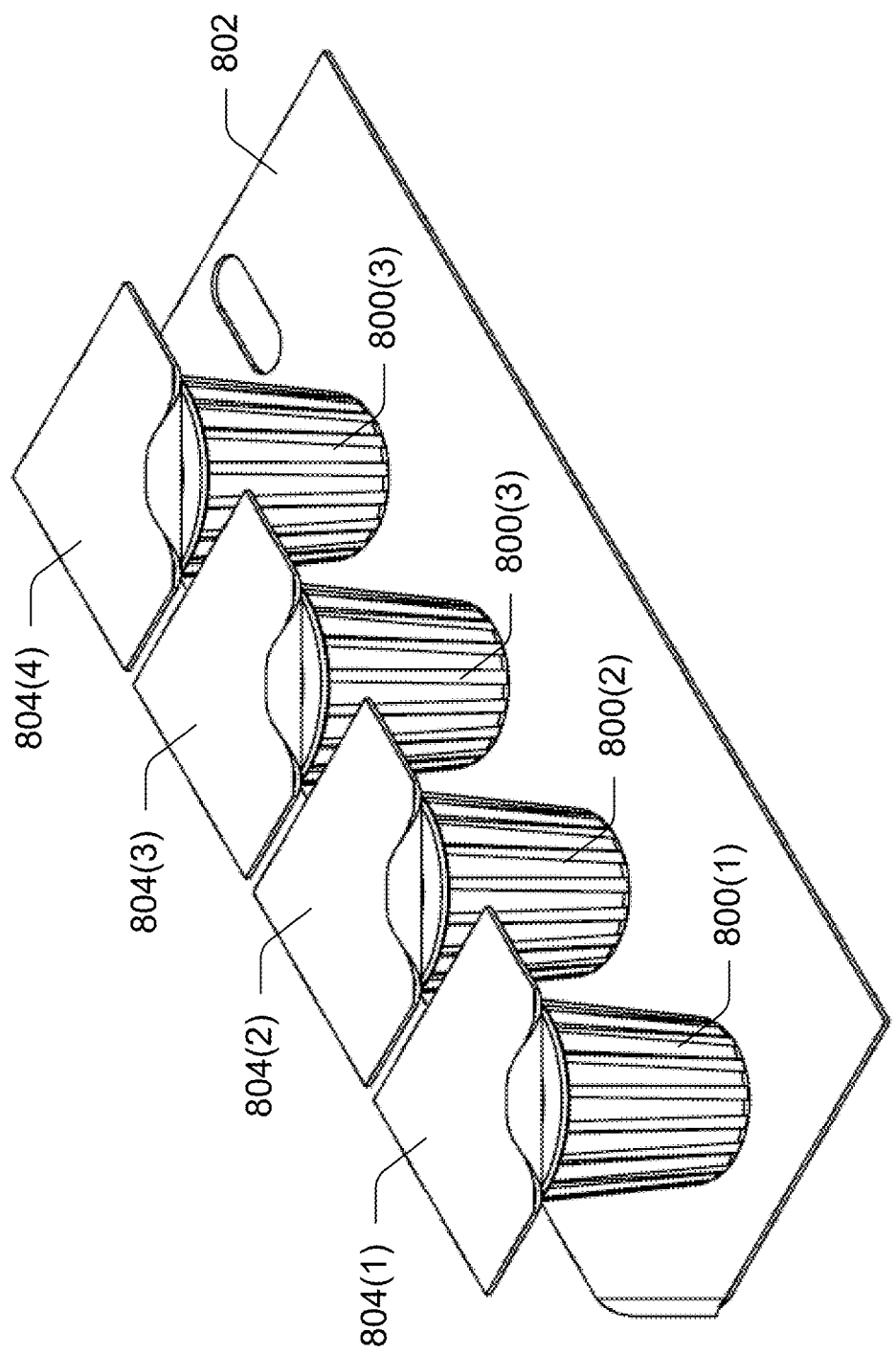
FIG. 8 illustrates an example configuration and packaging of individually sealed single cap devices and/or dual cap devices.

FIG. 8 illustrates an example configuration and packaging of individually sealed applicators and cap devices. As illustrated, individually sealed cap devices 800(1)-(4) are attached to a substrate (e.g., a strip or a sheet of material) 802 at an end opposite the end sealed by protective film 804(1)-(4), respectively. In some embodiments, any number of cap devices may be attached to the substrate 802. For example, the substrate 802 may include two cap devices or 100 cap devices. In some embodiments, the individually sealed cap devices 800(1)-(4) may be single cap devices as shown and described in reference to FIGS. 1-4. In other embodiments, the individually sealed cap devices 800(1)-(4) may include the individually sealed dual cap devices shown and described with reference to FIGS. 5-7. In some embodiments, the individually sealed cap devices 800(1)-(4) on the substrate 802 may be the same cap devices (i.e., all single cap devices); however, in some embodiments, the individually sealed cap devices 800(1)-(4) on the substrate 802 may be a combination of different cap devices (i.e., one or more single cap devices and one or more dual cap devices).

While FIG. 8 illustrates the cap devices in a single row, other embodiments may include two or more cap devices in a row across the substrate 802. In some embodiments, each cap device 800(1)-(4) may be attached to substrate 802 on a cap device surface other than the end opposite a cavity end sealed by protective film 804(1)-(4). For instance, each of the individually sealed cap devices 800(1)-(4) may be attached to the substrate 802 by a side surface of the cap devices 800(1)-(4). In some embodiments, each individually sealed cap device 800(1)-(4) may be attached to substrate 802 by an adhesive, sonic welding, microwave welding, thermal bonding, or the like.

In some embodiments, the substrate 802 may be composed of a flexible, rollable thermoplastic material. Individually sealed cap devices may then by dispensed by cutting between the cap devices 800(1)-(4) in the substrate 802. Alternatively, the substrate 802 may include perforations or score lines between the individually sealed cap devices in the substrate 802.

In other embodiments, the individually sealed cap device 800(1)-(4) may be attached to the substrate 802 by an end of the opening covered by the protective film 804(1)-(4). For instance, each protective film 804(1)-(4) may be bonded to the substrate 802 such that each cap device 800(1)-(4) may be peeled away or otherwise removed from the substrate 802 while the protective film 804(1)-(4) remains on each respective cap.

Figure 9:
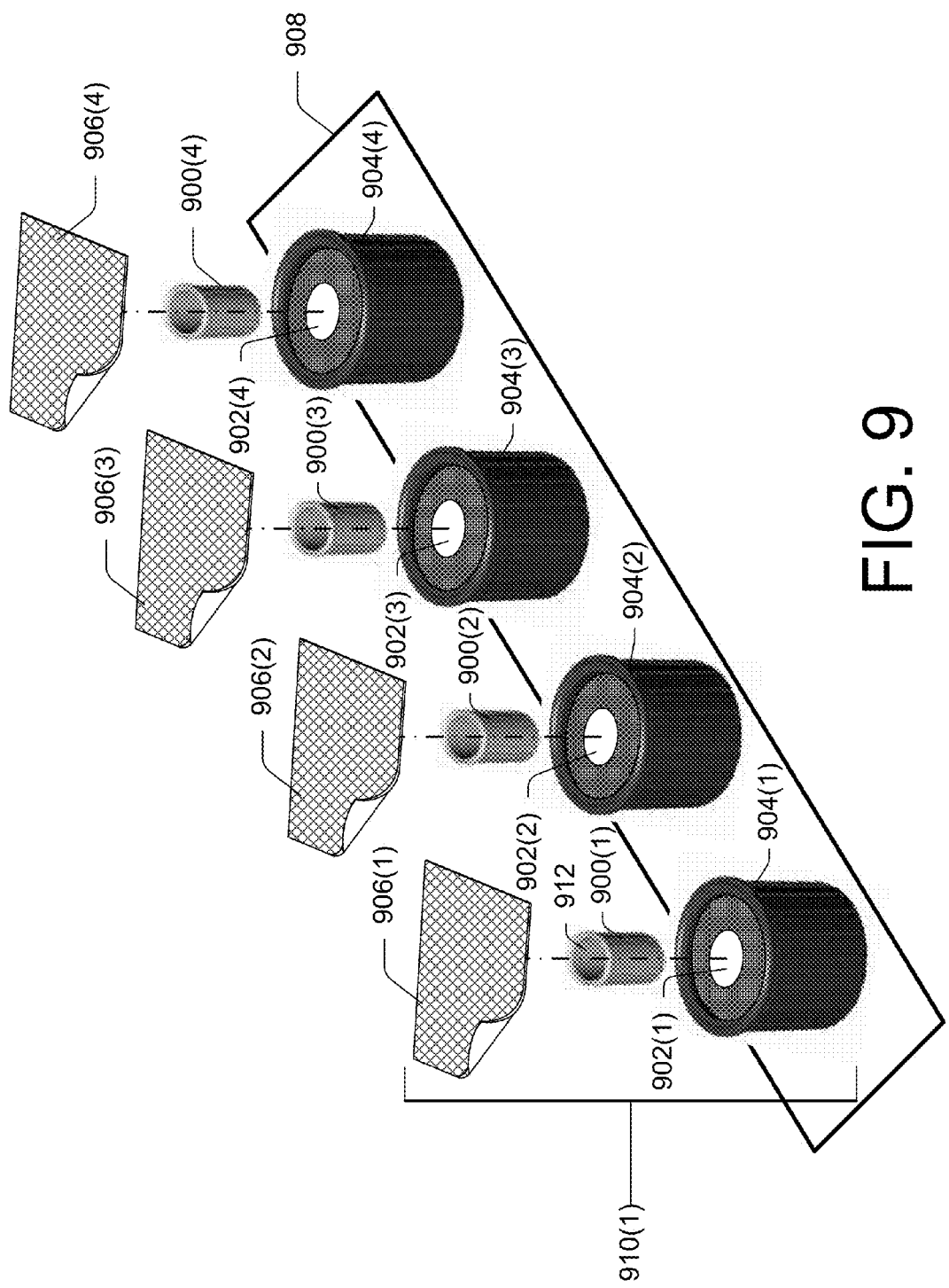
FIG. 9 illustrates an example embodiment of individually sealed applicators and cap devices used in dual cap devices and a configuration and packaging of such.

FIG. 9 illustrates another example embodiment in which first cap devices 900(1)-(4) may be removably stored within a cavity 902(1)-(4) of second cap devices 904(1)-(4), respectively, and sealed with protective films 906(1)-(4), respectively, to create a dual cap device 910(1). FIG. 9 further illustrates each individually sealed dual cap device may be attached to a substrate 908.

In some embodiments, both of the first cap devices 900(1)-(4) and the second cap devices 904(1)-(4) may include an applications material and/or a composition. In some embodiments, both of the first cap devices 900(1)-(4) and the second cap devices 904(1)-(4) may include a protective film to prevent contamination of the cavity of each respective cap device when sealed.

In some embodiments, the individually sealed dual cap device 910(1) may be removed from the substrate 908. In some embodiments, the protective film 906(1) may be removed from the second cap device 904(1) to expose the cavity 902(1) which secures the first cap device 900(1). In some embodiments, the cavity 912 of the first cap device may be secured to a first surface (e.g., female LUER-LOK® connector of an intravascular line port, a catheter, or the like) by manipulating an exterior surface of the second cap device 904(1) while the first cap device 900(1) is in the cavity 902(1). Upon the first cap device 900(1) being secured to the first surface, the cavity 902(1) may release the first cap device 900(1). In some embodiments, the second cap device 904(1) may then be used to clean and/or protect a second, different surface such as a port, vial, syringe, an injection site, or other component (e.g., male LUER-LOK® connector of an intravascular line port, a catheter, or the like). In some embodiments, the second cap device 904(1) may securely attach to the second, different surface.

CONCLUSION

Although the disclosure describes embodiments having specific structural features and/or methodological acts, it is to be understood that the claims are not necessarily limited to the specific features or acts described. Rather, the specific features and acts are merely illustrative some embodiments that fall within the scope of the claims of the disclosure.

What is claimed is:

1. An apparatus, comprising:
a plurality of medical cap devices removably adhered to a substrate, each medical cap device including:
a first medical cap having a cavity defined by an opening at a bottom end and a closed top end opposite the opening at the bottom end,
a protective film secured to the bottom end securing an applicator material containing a cleansing, antiseptic, or antimicrobial agent within the cavity, and
a second medical cap that is smaller than the first medical cap and is disposed within the cavity of the first medical cap,
wherein each medical cap device is removably adhered to the substrate by the closed top end of the first medical cap.

2. The apparatus as recited in claim 1, wherein the substrate comprises a flexible thermoplastic material.

3. The apparatus as recited in claim 1, wherein the protective film comprises a flexible, gas impermeable, liquid impermeable, pore-free material.

4. The apparatus as recited in claim 1, wherein the second medical cap comprises a cavity covered with a removable protective film securing an applicator material containing a cleansing, antiseptic or antimicrobial agent within the second cavity.

5. The apparatus as recited in claim 1, further comprising:
the applicator material containing the cleansing, antiseptic or antimicrobial agent within the cavity of the first medical cap;
wherein the cleansing, antiseptic or antimicrobial agent comprises:
about 5 to about 50 mg/ml of ethylenediaminetetraacetic acid (EDTA);
at most about 70% ethanol, by volume;
at most about 7.5% hydrogen peroxide, by volume; and water.

6. A medical cap device comprising:
a first cap having a cavity, the cavity containing an applicator material;
a second cap having a cavity, the cavity of the second cap containing the first cap and an applicator material or an antimicrobial composition; and
a film over the cavity of the second cap securing the first cap within the cavity of the second cap,
wherein the applicator material of the first cap is deformable and maintained in a compressed state while the first cap is secured within the cavity of the second cap.

7. The device as recited in claim 6, wherein a plurality of the medical cap devices are removably attached to a substrate by a surface opposite the cavity of the second cap.

8. The device as recited in claim 6, wherein the applicator material of the first cap and the applicator material of the second cap comprises starch polymer, cellulosic gel, polyethylene foam, polyurethane foam, silicone open cell foam, or mixtures thereof.

9. The device as recited in claim 6, wherein the applicator material of the first cap and applicator material of the second cap comprises a permeable material with different surface treatments, finishes, contours, or combinations thereof.

10. The device as recited in claim 6, wherein an antimicrobial composition of the first cap and the antimicrobial composition of the second cap are different concentrations of a composition comprising:

from about 5 mg/mL to about 50 mg/mL of ethylenediamine tetraacetic acid (EDTA), acids of EDTA, salts of EDTA, citrate, salts of citrate or any combination thereof;

from about 20% to about 70% by volume of ethanol;

from about 0.5% to about 7.5% by volume of hydrogen peroxide; and water.

11. A plurality of medical devices, each medical device comprising:
a first cap having a cavity holding an applicator material permeated with a cleansing, antiseptic or antimicrobial agent,
a second cap having a cavity holding an applicator material permeated with a cleansing, antiseptic or antimicrobial agent,
wherein the first cap is sealed within the cavity of the second cap by a film over the cavity of the second cap; and
wherein each medical device is attached consecutively to a substrate by a surface of the second cap other than an opening of the cavity.

12. The devices of claim 11, wherein the cleansing, antiseptic or antimicrobial agent of the first or second cap comprises a surfactant, water, a low molecular weight alcohol, a peroxide or peroxide-generating agent or a chelating agent.

13. The devices as recited in claim 11, wherein the cavity of the first cap and the cavity of the second cap include the cleansing, antiseptic or antimicrobial agent in a gel form.

14. The devices as recited in claim 11, wherein the substrate comprises a flexible thermoplastic material.

15. The devices as recited in claim 11, wherein the cavity of the second cap comprises one of a tapered stepped surface, a tapered smooth surface, a stepped surface, or threads.

16. The devices as recited in claim 11, wherein the cavity of the first cap is sealed with a film while sealed within the cavity of the second cap.

17. The apparatus as recited in claim 1, wherein the first medical cap includes an attachment feature that allows a user to engage the first medical cap to a connector surface.

18. The apparatus as recited in claim 17, wherein the attachment feature of the first medical cap includes one of: a threaded inner surface of the cavity; a flange disposed along a bottom surface of the opening and extending away from the opening of the first medical cap; or a flange on an inner surface at the opening of the cavity.

19. The apparatus as recited in claim 17, wherein the attachment feature of the first medical cap includes one of: a stepped inner surface of the cavity having an inner diameter, the inner diameter capable of matching an outer diameter of the connector surface; or a tapered continuous smooth inner surface.

* * * * *